United States Patent [19]

Barger

[11] Patent Number: 5,559,275
[45] Date of Patent: Sep. 24, 1996

[54] PROCESS FOR THE CONVERSION OF LOWER ALCOHOLS TO HIGHER BRANCHED OXYGENATES

[75] Inventor: Paul T. Barger, Arlington Heights, Ill.

[73] Assignee: UOP, Des Plaines, Ill.

[21] Appl. No.: 391,892

[22] Filed: Feb. 21, 1995

[51] Int. Cl.$^6$ .......................... C07C 27/00; C07C 29/34; C07C 31/12; C07C 41/09
[52] U.S. Cl. .......................... 568/905; 568/403; 568/485; 568/487; 568/671
[58] Field of Search .......................... 568/905, 487, 568/485, 403, 671

[56] References Cited

U.S. PATENT DOCUMENTS

| 1,910,582 | 5/1933 | Wibaut | 568/905 |
| 2,720,547 | 10/1955 | Wolff et al. | 260/614 |
| 2,971,033 | 2/1961 | Farrar et al. | 260/642 |
| 3,972,952 | 8/1976 | Clark | 260/642 |
| 4,219,678 | 8/1980 | Obenaus et al. | 568/697 |
| 4,304,943 | 12/1981 | Bjornson | 568/403 |
| 4,533,775 | 8/1985 | Fox et al. | 568/905 |
| 4,935,538 | 6/1990 | Budge et al. | 568/905 |
| 5,095,156 | 3/1992 | Radlowski et al. | 568/905 |

FOREIGN PATENT DOCUMENTS

0335092A2   10/1989   European Pat. Off. .

OTHER PUBLICATIONS

Lietti, Luca et al., "Synthesis of C$^+$Oxygenates from Methanol at Atomspheric Pressure over Alkali–promoted Zinc–Cromium Oxide Catalyststs," *Applied Catalysis*, vol. 70, (1991), pp. 73–86.

Obenaus, F. et al., "Huels–Process: Methyl Tertiary Butylether", presented at *The American Institute Of Chemical Engineers*, 85th National Meeting, Jun. 4–8, 1978.

Keim, Wilhelm and Falter, Wolfgang, "Isobutanol from Synthesis Gas." *Catalysis Letters*, vol. 3 (1989), pp. 59–63.

Ueda, Wataru et al., "A Low Pressure Guerbet Reaction over Magnesium Oxide Catalyst." *Journal Of Chemical Society Chemical Communication*, (1990), pp. 1558–1559.

Reddy, B. Mahipal et al., "A Single–Step Synthesis of Isobutyraldehyde from Methanol and Ethanol over CaO–ZnO–Al$_2$O$_3$ Catalyst." *Journal of Chemical Society Chemical Communication*, (1992), pp. 997–998.

Reddy, B. Mahipal et al., "Synthesis of Isobutyraldehyde from Methanol and Ethanol over Mixed Oxide Supported Vanadium Oxide Catalysts." *Applied Catalysis A: Genereral*, vol. 96, (1993), pp. L1–L5.

Wang, Fey–Long et al., "Catalytic Synthesis of Isobutyraldehyde from Methanol and n–Propyl Alcohol over Titanium Oxide–Supported Vanadium Oxide Catalysts." *Industrial Engineering Chemistry Research*, vol. 32, (1993), pp. 30–34.

*Primary Examiner*—Joseph E. Evans
*Attorney, Agent, or Firm*—Thomas K. McBride; John G. Tolomei; Richard P. Silverman

[57] ABSTRACT

A process is provided for the production of branched C$_{4+}$ oxygenates from lower alcohols such as methanol, ethanol, propanol and mixtures thereof. The process comprises contacting the lower alcohols with a solid catalyst comprising a mixed metal oxide support having components selected from the group consisting of oxides of zinc, magnesium, zirconia, titanium, manganese, chromium, and lanthanides, and an activation metal selected from the group consisting of Group VIII metal, Group IB metals, and mixtures thereof. The advantage of the process is improved yields and selectivity to isobutanol which can subsequently be employed in the production of high octane motor gasoline.

15 Claims, No Drawings

PROCESS FOR THE CONVERSION OF LOWER ALCOHOLS TO HIGHER BRANCHED OXYGENATES

The U.S. Government has a paid-up license in this invention and the right in limited circumstances to require the patent owner to license others on reasonable terms as provided for by the terms of contract No. DE-AC22-91PC90042 awarded to the Department of Energy.

FIELD OF THE INVENTION

The process of the present invention relates to the production of higher branched oxygenates from lower molecular weight alcohols. More particularly, the present invention relates to the contacting of lower molecular weight alcohols such as methanol, ethanol, and the like with a solid catalyst. Most particularly, the present invention relates to a solid catalyst for the conversion of lower molecular weight alcohols to higher branched alcohols wherein the solid catalyst comprises an activator metal and a mixed metal oxide support.

BACKGROUND OF THE INVENTION

Ethers and alcohols are high octane components which contribute significantly to the quality of motor gasoline. The introduction of ethers and alcohols into motor gasoline as part of gasoline reformation generally increases the amount of oxygen in the gasoline. This additional oxygen combined with restrictions on aromatic hydrocarbons and heavy metals in finished gasoline is expected to result in the reduction of ozone-forming volatile organic compounds, exhaust nitrogen oxide emissions, and toxic emissions from motor vehicle exhaust.

High octane ethers for motor gasoline production are generally produced by a combination of an isoolefin with a monohydroxy alcohol such as methanol or ethanol in an etherification process. The etherification process can also be used as a means to produce pure isoolefin by cracking of the product ether. For instance, pure isobutylene can be obtained for the manufacture of polyisobutylenes and tert-butylphenol by cracking methyl tertiary butyl ether (MTBE). The production of MTBE has emerged as a predominant etherification process which uses $C_4$ isoolefin as the feedstock. A detailed description of processes, including catalyst processing conditions, and product recovery, for the production of MTBE from isobutylene and methanol are provided in U.S. Pat. Nos. 2,720,547 and 4,219,678 and in an article at page 35 of the Jun. 25, 1979, edition of Chemical and Engineering News. The preferred process is described in a paper presented at The American Institute of Chemical Engineers, 85lh National Meeting on Jun. 4-8, 1978, by F. Obenaus et al. The above references are herein incorporated by reference. Other etherification processes of current interest are the production of tertiary amyl methyl ether (TAME) by reacting $C_5$ isoolefin with methanol, and the production of ethyl tertiary butyl ether (ETBE) by reacting $C_4$ isoolefins with ethanol.

The problem with producing ethers from isoolefin is that the feedstock is usually derived from a petroleum or natural gas stream which must first be converted into an isoparaffin, followed by the alehydrogenation of the isoparaffin to an isoolefin, and finally, the etherification of the isoolefin with alcohol. Processes are sought which provide more direct lower cost routes to such ethers.

Alternatives to petroleum based technologies are sought as a route to high octane blending components for motor gasoline and reformulated gasoline having an increased content of oxygenates. A number of approaches to producing higher branched oxygenales such as $C_4^+$ alcohols and aldehydes have been attempted by converting a synthesis gas comprising a carbon oxide and hydrogen in a simple step process. These processes have generally been characterized by severe operating conditions, low conversion, and low catalyst selectivity to the branched oxygenate product. An example of this approach is found in EPO patent application 0,335,092. European Patent Application 0,335,092A2 to W. Falter et al. discloses a method of producing alcohol mixtures with an increased portion of isobutanol directly from synthesis gas such as CO and $H_2$, or $CO_2$ and $H_2$, or mixtures of $CO_2$ and CO with $H_2$ or other gases containing CO, $CO_2$ and $H_2$ over a catalyst comprising a base of zirconium, zinc, and manganese oxides and up to 10 wt % of a base compound. The base compound may include an alkali and/or an alkaline-earth metal and/or ammonia. In addition, the catalyst may contain from 0.01 to 2 wt % palladium in elemental or compound form. Other metals such as Au, Ag, Cu, Sc, Y, Lanthanides, Ru, Rh, Os, Ir, and Pt are also disclosed as elements which can be contained in the catalyst. The reaction takes place at temperatures of 420°–825° C. and pressures between 10 and 480 bar. The catalyst is prepared by co-precipitation or successive precipitation of the corresponding metal salt solutions such as nitrates. In a related article entitled, "Isobutanol from Synthesis Gas," published in *Catalysis Letters*, Vol. 3 (1989), pages 59–63, the same inventors disclose an active and selective Zr—Zn—Mn—Li—Pd catalyst for a one-step synthesis of isobutanol from synthesis gas. They suggest that the use of palladium increases the selectivity to isobutanol by favoring methanol synthesis and suppressing methane formation. They particularly point out that at pressures less than 10 MPa, the isobutanol selectivity decreases, favoring methane formation. They also point out the critical nature of the temperature influence on isobutanol. At 645° K., the isobutanol yield is 4%, but at 715° K., the isobutanol yield increases to 45%. At higher temperatures the isobutanol yield decreases.

Other approaches to the production of higher branched oxygenates have focused on a two-step process wherein the first stage is the conversion of synthesis gas by well-known methods to methanol and the second step is the conversion of methanol to higher branched alcohols. Examples of such approaches are characterized by the vapor phase conversion of a mixture of methanol and ethanol over a solid catalyst employing a condensation reaction. Generally, these approaches have not provided the catalyst activity and selectivity levels necessary to offer a commercially viable route from methanol to the higher branched oxygenates. In addition, none of the approaches have demonstrated the ability to provide higher catalyst activity for the conversion of methanol in the absence of ethanol to produce such higher branched oxygenates as isobutanol.

U.S. Pat. No. 5,095,156 to Radlowski et al. relates to a continuous vapor phase condensation process to convert a $C_2$ or higher alcohol, and one or more $C_1$ or higher alcohols to a mixture containing at least one higher molecular weight alcohol such as butanol over a catalyst which is essentially magnesium oxide. The magnesium oxide component may, in addition, be supported by titania, alumina, silica, boria, zirconia, and a carbonaceous material such as charcoal. The isobutanol produced by the condensation reaction is separated, dehydrated, and reacted with additional methanol to form MTBE. In a related work by Wataru Ueda, Tetsuo Kawabara, Talmo Ohshida and Yutaka Morikawa, published in the Japanese Chemical Society, Chemical Communications, on pages 1558–1559 (1990), disclosed a synthetic method for the production of higher alcohols from methanol over a magnesium oxide catalyst at atmospheric pressure and elevated temperature. Ueda indicated that magnesium oxide showed the best catalytic activity in the reaction of methanol and ethanol selectively yielding propan-1-ol and 2 methylpropan-1-ol, zinc oxide catalyzed the alehydrogenation of ethanol to ethanol and zirconium oxide catalyzed the dehydration of alcohols to ethers. Magnesium oxide prepared by precipitation from magnesium nitrate was shown to exhibit poor activity and poor selectivity to higher alcohols.

In a paper entitled, "Synthesis of $C_2^+$Oxygenales from Methanol at Atmospheric Pressure over Alkali-promoted Zinc-Chromium Oxide Catalysts, " by Luca Lietti et al., which appeared in *Applied Catalysis*, Volume 70, pages 73–86, in 1991, zinc-chromium oxide based catalysts were disclosed for the synthesis of higher oxygenates from methanol and hydrogen. Lietti et al. found that potassium-promoted zinc-chromium oxide, while decomposing a large part of methanol to carbon monoxide and hydrogen, also produces $C_2^+$ oxygenates. Lietti et al. concluded that alkali addition plays a crucial role in the formation of $C_2^+$ oxygenates over the zinc-chromium oxide catalyst.

An article by B. Mahipal Reddy et al., entitled "A Single-Step Synthesis of Isobutyraldehyde from Methanol and Ethanol over CuO—ZnO—$Al_2O_3$ Catalyst," published in the *Journal of the Chemical Society*, Chemical Communication, pages 997–998, in 1992, discloses a catalyst for the production of isobutyraldehyde and its derivatives such as isobutanol over a CuO—ZnO—$Al_2O_3$ catalyst from mixtures of methanol and water. In a further development, Reddy et al. in an article entitled, "Synthesis of Isobutyraldehyde from Methanol and Ethanol Over Mixed Oxide Supported Vanadium Oxide Catalysts," published in *Applied Catalysis A: General*, volume 96, pages L1–L5, in 1993, discloses the use of mixed oxides including $TiO_2$—$Al_2O_3$, $TiO_2$—$SiO_2$, TiO2—ZrO: and $TiO_2$—$SiO_2$—$ZrO_2$ wherein the $V_2O_5$/$TiO_2$—$SiO_2$ catalyst showed the better total conversion and product selectivity.

An article by Fey-long Wang et al. entitled, "Catalytic Synthesis of Isobutyraldehyde from Methanol and n-Propyl Alcohol over Titanium Oxide—Supported Vanadium Oxide Catalysts, published in Industrial Engineering Chemistry Research, volume 32, pages 30–34, in 1993, disclosed a process for the synthesis of isobutyraldehyde which is a raw material for producing isobutyl alcohol. Fey-long Wang et al. selectively produce isobutyraldehyde from methanol and ethanol in one step by using titanium oxide-supported vanadium oxide as a catalyst.

U.S. Pat. No. 2,971,033 to Martin W. Farrar disclosed a process for the manufacture of higher molecular weight alcohols from alcohols of lower molecular weight by carrying out the reaction in the presence of potassium carbonate, magnesium oxide, and copper chromite. The reaction was characterized by low conversions.

U.S. Pat. No. 3,972,952 to Roger T. Clark discloses a solid catalyst composition for the vapor phase conversion of methanol and ethanol to higher linear alcohols, particularly n-propanol, over a catalyst comprising 85–97% alumina and 2–14% of a base promotor selected from the group of oxides, hydroxides, and basic salts of alkali and alkaline earth metals with between 0.1 and 1 percent of a platinum group metal such as ruthenium, rhodium, palladium, osmium, iridium, and platinum. The process was carried out at a temperature range of about 200° C. to 400° C. and a pressure between about 6.7 MPa to about 33 MPa (1000 and 5000 psig) and space velocity of about 2000 to about 10,000 $hr^{-1}$, but produced very small amounts of isobutanol.

U.S. Pat. No. 4,533,775 to Joseph R. Fox et al. discloses a process for the upgrading of lower alcohols to higher molecular weight alcohols by contacting the lower alcohol with a reaction promotor having a composition including a metal acetylide and a methyl hydride, and mixtures thereof.

Thus, the conversion of syngas to isobutanol, which can be readily dehydrated to isobutene, has received a significant amount of interest in the past several years. The major effort has focussed on the direct conversion of syngas to isobutanol, generally using catalysts based on alkali-modified methanol synthesis catalysts. Typically, the productivities of these catalysts are low (<100 g isobutanol/kg catalyst/hr) and they co-produce methanol in amounts exceeding the stoichiometric requirement for the production of MTBE. In contrast, conventional methanol synthesis produced methanol with >99% selectivity and productivities of > 1000 g methanol/kg catalyst/hr. The present invention has focussed on the development of a new process that can be used to convert lower alcohols to isobutanol. Processes are sought for the conversion of lower alcohols to higher, branched oxygenates such as isobutanol which provide the activity and selectivity of a commercially viable process.

SUMMARY OF THE INVENTION

The present invention represents the discovery that lower molecular weight alcohols can be converted directly to higher, branched oxygenates such as isobutanol over a catalyst comprising mixed metal oxide support and an activator metal. Furthermore, it was found that the conversion of lower molecular weight alcohols to isobutanol can occur at relatively moderate conditions while providing improved yields and selectivity to isobutanol. With this new process, the route from synthesis gas to isobutanol can be accomplished in two-steps wherein the first step employs well-known and established routes from synthesis gas to methanol followed by tile present process to convert the methanol to isobutanol. The isobutanol produced by the present invention may be subsequently converted to ethers such as MTBE by other well-known methods. Thus, the present invention provides a long sought bridge to the establishment of a viable path from synthesis gas, derived from coal, natural gas, or biowaste, to high octane motor gasoline.

In accordance with the present invention, a process is provided for the conversion of a feedstock comprising lower alcohols such as methanol, ethanol, and propanol to higher branched oxygenates comprising isobutanol. The process comprises contacting the feedstock with a solid catalyst at conditions favoring the conversion of lower alcohols to the higher branched oxygenates. The solid catalyst comprises a mixed metal oxide support having at least two components selected from the group consisting of oxides of zinc, magnesium, zirconium, titanium, manganese, chromium, and, lanthanides, such as cerium and lanthanium; and, an activator metal selected from Group VIII or Group IB. A metal cation selected from the group consisting of sodium, potassium, calcium, magnesium, and mixtures thereof optionally may be incorporated.

DETAILED DESCRIPTION OF THE INVENTION

The lower alcohols include methanol, ethanol, and propanol. An especially preferred lower alcohol is methanol.

The higher branched oxygenates include $C_4$-$C_{20}$ alcohols, aldehydes, ketones, and ethers. The preferred higher branched oxygenates are $C_4$-$C_8$ alcohols, and aldehydes, ketones, and ethers, and the most preferred higher branched oxygenates are $C_4$-$C_6$ alcohols, particularly isobutanol, and $C_4$-$C_6$ aldehydes, particularly isobutyraldehyde. The feed to the process, in addition, may contain small amounts of one or more of methane, oxygen, nitrogen, hydrogen, carbon monoxide, and carbon dioxide.

It is generally accepted that the condensation of methanol to isobutanol occurs by an aldol condensation mechanism. The key C—C bond forming steps are believed to be catalyzed by basic sites on the metal oxide surface. Methanol is converted sequentially via ethanol and n-propanol intermediates to the desired isobutanol product by $C_1$ chain growth. The initial step of methanol to ethanol, by $C_1$ growth at the first carbon atom to the hydroxyl group, is substantially slower than the subsequent steps which involve bond forming at the second atom. These relative rates result in the observed high selectivity to methanol and isobutanol in direct syngas conversion to higher alcohols. It has also been suggested that aldehyde intermediates may also be important in this reaction pathway. Small amounts of non-alcohol products such as aldehydes, ethers, and ketones generally also occur in the product.

The condensation of 4 equivalents of methanol to 1 equivalent of isobutanol also produces 3 equivalents total of $H_2O$ and $CO_2$. The production of water is preferred since it does not result in a loss of carbon. However, the catalysts used in this process generally catalyze the water gas shift reaction which equilibrates these by-products, favoring $CO_2$ at reaction conditions used. Thus, $CO_2$ is a stoichiometric product of methanol condensation. On the other hand, CO is viewed as an undesired by-product arising from the decomposition of methanol back to synthesis gas.

The catalyst of the present invention comprises mixed metal oxide support, including oxides from Group VIIB, Group VIB, Group IVB and Group IIB of the Periodic Table. Preferably the mixed metal oxide support is selected from the group consisting of zinc oxide, manganese oxide, zirconium oxide, titanium oxide, chromium oxide, lanthanide oxides, and mixtures thereof. Preferably the lanthanide oxides include the oxides of cerium and lanthanide. Preferably, the manganese oxide is present in the mixed metal oxide support as less than about 80 molar percent, and more preferably the manganese oxide is present in a range between about 10 and 60 molar percent, and most preferably the manganese oxide is present in a range of about 20 to 40 molar percent. In addition to the manganese oxide, it is preferred that the mixed metal oxide support contain between about 10 and about 60 molar percent zinc oxide, and more preferably in addition to the manganese oxide, the zinc oxide will be present in a range between about 20 and about 45 molar percent. In addition manganese oxide and zinc oxide, it is preferred that the mixed metal oxide support contains between 10 and 60 molar percent of zirconium oxide or cerium oxide, and it is more preferred that the mixed metal oxide support contains between 10 and 45 molar percent of zirconium oxide or cerium oxide.

The catalyst support further comprises an optional metal cation of an alkali metal or an alkaline earth metal. Preferably the metal cation is selected from the group consisting of sodium, potassium, calcium, magnesium, and mixtures thereof.

The catalyst further comprises an activation metal selected from the group consisting of palladium, platinum, nickel, silver, rhodium, cobalt, and mixtures thereof. More preferably, the activator metal is selected from the group consisting of platinum, palladium, and mixtures thereof. It is preferred that the activator metal be present in an amount ranging from about 0.2 to about 5 wt percent. More preferably, the activator metal will be present in an amount ranging from about 0.5 to about 5 wt percent, and most preferably the activator metal will be present at about 2.0 wt percent.

The catalyst of the present invention may be prepared by the calcination of the hydroxide or carbonate of selected metals to produce a mixed metal oxide support followed by the impregnation of the mixed metal oxide support with an activator metal. However, to more effectively produce a catalyst with a homogeneous distribution of metal oxides, it is preferred to prepare the mixed metal oxide support by co-precipitation of metal salts with a basic compound to provide a precipitate having the desired molar percentage of metal oxides. In addition, mixed metal oxides produced in this manner will contain a metal cation such as sodium, potassium, calcium, or magnesium when a metal hydroxide solution is employed to affect the precipitation. The precipitate is impregnated with an activator metal in the conventional manner. It is preferable to calcine the precipitate prior to impregnation with a salt solution of the activator metal and to recalcine the precipitate following impregnation.

Use of a carrier gas mixed with the feed to the process can be advantageous. Such materials as hydrogen, carbon monoxide, carbon dioxide, a hydrocarbon, and inert gases such as nitrogen, argon, and the like may be used to improve the condensation reaction. The use of hydrogen in the process can improve selectivity and, if used, is generally employed in a hydrogen/feed ratio of from about 20:1 to about 1:1, more preferably, about from 10:1 to about 1:1.

The catalyst, with or without a carrier gas added to the feed, can be used in a fixed bed, ebullated bed, fluidized bed, or other type of vapor phase process. A copper-walled reactor has been found to be beneficial. In general, the temperature range useful in carrying out the condensation reaction described herein runs between about 300° and about 700° C., more preferably, between about 300°and about 500° C., and most preferably between about 300° and 400° C. The range of total reactor pressure useful in this invention runs between subatmospheric and about 3.4 MPa (500 psia), more preferably, between atmospheric and about 1000 kPa (145 psia), and most preferably, atmospheric to about 200 kPa (30 psia). Useful weight hour space velocities run between about 0.05 and about 50 $hr^{-1}$, and more preferably, between about 0.05 and about 10 $hr^{-1}$ based upon the flow rate of methanol in the feed.

A process which may be carried out employing the condensation :reaction is the production of MTBE from synthesis gas as the sole carbon source. In such a process, synthesis gas is converted to methanol. The methanol is subsequently condensed over the catalyst described herein at the above conditions to form a mixture of higher branched oxygenates rich in isobutanol. The isobutanol may then be separated from the mixture, dehydrated, and reacted with additional methanol to form MTBE.

EXAMPLES

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

All catalysts were evaluated in a fixed bed, continuous, down flow, (13 mm I.d.) stainless steel reactor. Approximately 5 grams of each catalyst as 20–40 mesh granules were loaded into the reactor to form the catalyst bed and was supported above and below by inert quartz chips. Prior to each catalyst evaluation, the reactor was first purged with nitrogen at 250 ° C. and 170 kPa (24.7 psia) for 1 hour and then pressure tested with nitrogen at 250° C. and 3.5 MPa (5.15 psia) for 1 hour. The nitrogen purge was restarted and the temperature and pressure were adjusted to desired conditions. After 2 hours, the feedstock, comprising a 10/1 molar mixture of methanol/ethanol, was charged to the reactor at the desired rate for 16 hours. Product analyses were obtained by 2 on-line gas chromatographs to analyze the total hydrocarbon and oxygenate product and the overhead gas. Conversions, selectivities and productivities are based on moles of carbon and reflect the average values between 8 and 16 hours on stream.

EXAMPLE I

A mixed metal oxide solution was prepared by dissolving 949 gms of a 14.8 wt-% zirconium oxynitrate solution, 460 gins of zinc nitrate, and 443 gins of manganese nitrate in about 2 liters of distilled water. Approximately 4000 ml of a 3.75M solution of potassium hydroxide was added to the mixed metal oxide solution at a temperature of about 50° C. and a pH of about 11 to form a solid precipitate. The solid precipitate was water washed with distilled water and dried at a temperature of 127° C. for about 15 hours. The dried precipitate was sized by conventional means to 20–40 mesh particles and calcined at 327° C. in air for about 3 hours. The resulting solid mixed metal oxide catalyst contained an equimolar mixture of Zr, Zn, and Mn.

EXAMPLE II

A portion of the mixed metal oxide catalyst prepared according to the procedure of Example I was impregnated with palladium by contacting 25 gms of solid mixed metal oxide catalyst with about 1.8 gms of an aqueous 2.78M $PdCl_2$ solution diluted to about 40 ml with water, evaporating to dryness, and recalcining the solid at about 400° C. in air to provide a mixed metal oxide catalyst having about 0.2 wt-% Pd.

EXAMPLE III

A portion of the mixed metal oxide catalyst prepared according to the procedure of Example I was impregnated with about 18 gms of the aqueous $PdCl_2$ solution of Example I diluted to 40 ml with water and calcined according to the procedure of Example II to provide a mixed metal oxide catalyst having about a 2.1 wt-% Pd.

EXAMPLE IV

A portion of the mixed metal oxide catalyst of Example I was impregnated with platinum by contacting 15 gms of the mixed metal oxide catalyst with 11.6 gms of an aqueous solution of 2.59M $PtCl_2$ diluted to 25 ml with water and re-calcining the solid at about 450° C. in air to provide a mixed metal oxide catalyst having about 2.0 wt-% platinum.

EXAMPLE V

A mixed metal oxide catalyst having about 2.0 wt-% silver impregnated thereon was prepared according to the procedure of Example IV using an aqueous solution of silver nitrate.

EXAMPLE VI

A mixed metal oxide solution was prepared by dissolving 297 gins of zinc nitrate, 287 gms of manganese nitrate, and 403 gms of chromium nitrate according to the procedure of Example I to provide a solid mixed metal oxide catalyst having Zn, Mn, and Cr present in a molar ratio of 34/33/33.

EXAMPLE VII

The process of Example IV was employed to impregnate a portion of the Zn/Mn/Cr solid catalyst of Example VI with about 2.0 wt-% platinum.

EXAMPLE VIII

The process of Example III was employed to impregnate a portion of the Zn/Mn/Cr solid catalyst of Example VI with about 2.0 wt-% palladium.

EXAMPLE IX

A mixed metal oxide solution was prepared by dissolving 310 gms of zinc nitrate, 294 gms of manganese nitrate, and 451 gins of cerium nitrate and precipitated with potassium hydroxide solution according to the procedure of Example I to provide a solid mixed metal oxide catalyst having Zn, Mn, and Ce present in a molar ratio of 34/33/33.

EXAMPLE X

The process of Example IV was employed to impregnate a portion of the Zn/Mn/Ce solid catalyst of Example IX with about 2.0 wt-% platinum.

EXAMPLE XI

The mixed metal oxide catalysts of Examples I–X were evaluated in a fixed bed reactor according to the procedure described hereinabove for the ability to convert a feedstock having a 10/1 molar ratio of methanol to ethanol to isobutanol at a temperature of about 350° C., a pressure of about 308 kPa (45 psia), and a methanol weight hourly space velocity of about 2 $hr^{-1}$. Table 1 summarizes the results of the separate catalyst evaluations. The catalysts of Examples I and VI represent mixed metal oxide catalysts, but without the addition of a Group I or a noble metal.

In comparing the Zn/Mn/Zr material of Example I to the Zn/Mn/Cr composition of Example VI, it was found that the conversion of methanol, the selectivity to isobutanol, and the productivity to isobutanol were low and that the Zn/Mn/Zr material was significantly more active than the Zn/Mn/Cr material. Surprisingly, both catalyst materials, when impregnated with a nobel metal (Group VIII), showed significant improvement in conversion of the ethanol in the feed from about 50% to about 90+%. In addition, for the catalyst of Examples III and IV and Examples VII and VIII, the conversion of methanol improved by about 500% for the Zn/Mn/Zr base material and the conversion of methanol improved by about 1000+% for the Zn/Mn/Cr base material when platinum and palladium were impregnated at a level of about 2.0 wt-%. The addition of about 2.0 wt-% silver, a Group I metal of Example V, to the Zn/Mn/Zr base of Example I provided some productivity improvement, while the conversion of methanol and the selectivity to isobutanol remained relatively the same as the base in Example I. Clearly, the addition of about 2.0 wt-% platinum or palladium to the mixed metal oxide catalysts of Examples I and VI provided significant improvement to the conversion, the selectivity, and the productivity over the non-noble metal mixed metal oxide catalysts at these conditions. Furthermore, the conversion data indicate that ethanol is almost completely convened and that conversion of methanol continues following the disappearance of the ethanol.

impregnated with 2 wt-% Pt. The metal oxide composition ranged as follows:

Zn 10–60wt-%

Mn 10–60wt-%

Zr 10–60 wt-%

The mixed metal oxide catalyst bases were prepared according to the procedures of Example I with the amount of metallic nitrates selected to achieve the desired ratio of metal oxides in the calcined precipitate. The impregnation of these samples was performed according to the procedure of

TABLE 1

SUMMARY OF Zn/Mn/Zr AND Zn/Mn/Cr OXIDE CATALYSTS

| CATALYST EXAMPLE NO. | CONVERSION, % | | SELECTIVITY, MOL % | | | PRODUCTIVITY (g/Kg cat./hr) | |
|---|---|---|---|---|---|---|---|
| | METHANOL | ETHANOL | $iC_4OH$ | Tot. $C_{4+}$ | $CO_x$ | $iC_4OH$ | Tot. $C_{4+}$ |
| I. (Zn/Mn/Zr) Base | 9 | 50 | 13 | 18 | 14 | 13 | 18 |
| II. (0.2 Pd) | 30 | 88 | 8 | 21 | 35 | 1 | 1 |
| III. (2.1 Pd) | 51 | 99 | 8 | 41 | 37 | 62 | 328 |
| IV. (2.0 Pt) | 47 | 99 | 14 | 49 | 44 | 102 | 373 |
| V. (2.0 Ag) | 11 | 67 | 13 | 45 | 26 | 37 | 128 |
| VI. (Zn/Mn/Cr) Base | 5 | 43 | 1 | 36 | 31 | 2 | 72 |
| VII. (2% Pd) | 79 | 100 | 9 | 36 | 57 | 99 | 339 |
| VIII. (2% Pt) | 51 | 90 | 2 | 18 | 75 | 17 | 102 |
| X. (Zn/Mn/Ce)(2% Pt) | 50 | 100 | 12 | 46 | 48 | 91 | 349 |

EXAMPLE XII

Based on the improved performance of the mixed metal oxide catalysts with platinum for the conversion of methanol to isobutanol in Example XI, a series of single and double metal oxide catalysts impregnated with about 2.0 wt-% platinum were prepared according to the precipitation and calcination procedures of Example I from nitrates and the platinum impregnation steps of Example IV. For the zinc oxide and the zinc/manganese oxide catalysts, a 10% $SiO_2$ binder is incorporated into the precipitate by conventional means. Table 2 presents the results of the catalyst screening according to the methanol conversion reactor operation of Example IX. The zinc oxide catalyst, C, showed the lowest conversion of ethanol, with a corresponding low selectivity and productivity to isobutanol while favoring the decomposition of methanol to carbon oxides. The catalysts C, D, and E provide conversion to methanol at levels between 66 to 74 percent and corresponding isobutanol productivities of 65 to 83 gms per kilogram of catalyst per hour.

Example IV with 2 wt-% platinum. The Pt impregnated samples were evaluated according to the procedure of Example XI at a temperature of 350° C., a pressure of 308 kPa and a weight hourly space velocity of about 2 $hr^{-1}$. The ratio of nitrogen to methanol in the feed was 2:1 on a molar basis. The results of the catalyst screening for varying metal oxide compositions is shown in Table 3. These results indicate that the support has a surprisingly minor effect on the performance of the catalyst. The preferred oxygenate selectivities were obtained with zinc at or above 33 mole percent and correspondingly low zirconium molar ratios.

TABLE 2

MIXED METAL OXIDE CATALYSTS WITH 2 WT % PLATINUM

| CATALYST BASE | | CONVERSION, % | | SELECTIVITY | | | PRODUCTIVITY | |
|---|---|---|---|---|---|---|---|---|
| | | MeOH | ETOH | $iC_4OH$ | Tot. $C_{4+}$ | $CO_x$ | $iC_4OH$ | Tot $C_{4+}$ |
| A | $ZnO/SiO_2$ | 37 | 95 | 7 | 36 | 52 | 44 | 224 |
| B | $MnO_2$ | 36 | 83 | 2 | 14 | 77 | 9 | 63 |
| C | $ZrO_2$ | 46 | 53 | 0 | 2 | 85 | 0 | 13 |
| D | Z/Al (75/25) | 74 | 100 | 7 | 25 | 57 | 74 | 266 |
| E | Zn/Cr (75/20) | 66 | 100 | 9 | 30 | 58 | 83 | 289 |
| F | Zn/Mg (50/50) | 71 | 100 | 6 | 25 | 70 | 65 | 250 |

EXAMPLE XIII

The effect of varying the mixed metal oxide was evaluated by the preparation of a series of mixed metal oxide catalysts

TABLE 3

VARYING METAL OXIDE COMPOSITION AT 2% Pt

| METAL OXIDE COMPOSITION, MOL-% | | | CONVERSION Wt-% | | SELECTIVITY, |
| --- | --- | --- | --- | --- | --- |
| Zn | Mn | Zr | MeOH | EtOH | % iC$_4$OH |
| 60 | 20 | 20 | 58.7 | 100 | 11.1 |
| 45 | 10 | 45 | 68.3 | 100 | 8.0 |
| 45 | 45 | 10 | 63.6 | 100 | 10.4 |
| 34 | 33 | 33 | 57.3 | 99.8 | 10.8 |
| 20 | 20 | 60 | 59.0 | 99.4 | 8.9 |
| 20 | 60 | 20 | 69.9 | 100 | 8.2 |
| 10 | 45 | 45 | 73.3 | 100 | 8.9 |

EXAMPLE XIV

The variation of platinum impregnated in the mixed metal oxide support was evaluated over a range of 0.5 to 5 wt-%. The mixed metal oxide support having a 60/20/20 distribution of Zn/Mn/Zr of Example XIII were impregnated with platinum according to the procedures of Example IV to achieve all impregnation platinum levels. The resulting catalysts were evaluated at a reaction temperature of about 350° C. and a pressure of about 308 kPa, and a weight hourly space velocity of 2 hr$^{-1}$. Nitrogen was passed to the reactor in a molar ratio of 2:1 to the amount of methanol in the feed. The results are shown in Table 4. These results indicate that the 2 wt-% Pt loadings provide the highest isobutanol selectivity.

TABLE 4

VARYING PLATINUM IMPREGNATION ON MIXED METAL OXIDE SUPPORTS HAVING A 60/20/20 Mol-% DISTRIBUTION OF Zn/Mn/Zr

| Pt | CONVERSION, Wt-% | | SELECTIVITY, |
| --- | --- | --- | --- |
| WT-% | MeOH | EtOH | % iC$_4$OH |
| 0.5 | 68.5 | 100 | 8.5 |
| 1.0 | 71.6 | 100 | 9.2 |
| 2.0 | 58.7 | 100 | 11.1 |
| 5.0 | 67.6 | 99.8 | 8.2 |

We claim:

1. A process for the conversion of a lower alcohol selected from the group consisting of methanol, ethanol, propanol, and mixtures thereof to a higher branched oxygenate by aldol condensation, said process comprising contacting said lower alcohol at a reaction pressure ranging between atmospheric and about 200 kPa and a weight hour space velocity between about 0.05 and about 10 hr$^{-1}$ with a solid catalyst comprising:
   a) a mixed metal oxide support having at least two components selected from the group consisting of zinc oxide, magnesium oxide, zirconium oxide, manganese oxide, titanium oxide, chromium oxide, and a lanthanide oxide; and
   b) an activator metal selected from the group consisting of palladium, platinum, silver, rhodium, cobalt, and mixtures thereof.

2. The process of claim 1 wherein said solid catalyst further comprises a metal cation selected from the group consisting of sodium, potassium, calcium, magnesium, and mixtures thereof.

3. The process of claim 1 wherein said contacting takes place at a reaction temperature ranging from about 300° C. to about 500° C.

4. The process of claim 1 wherein the mixed metal oxide support comprises zinc oxide and manganese oxide.

5. The process of claim 4 wherein the zinc oxide comprises from about 10 to about 60 mole percent of the mixed metal oxide support.

6. The process of claim 4 wherein the manganese oxide comprises about 10 to 60 mole percent of the mixed metal oxide support.

7. The process of claim 4 wherein the activator metal comprises palladium.

8. The process of claim 4 wherein the activator metal comprises platinum.

9. The process of claim 4 wherein said mixed metal oxide support further comprises a zirconium oxide in an mount ranging from 10 to 60 mole percent of the mixed metal oxide support.

10. The process of claim 9 wherein said activator metal comprises platinum or palladium in an amount ranging from about 0.5 to about 5 wt-percent of said solid catalyst.

11. The process of claim 4 wherein said mixed metal oxide support further comprises a cerium oxide in an amount ranging from 10 to 60 mole percent of the mixed metal oxide support.

12. The process of claim 11 wherein said activator metal comprises platinum or palladium in an amount ranging from about 0.5 to about 5 wt-percent of said solid catalyst.

13. The process of claim 1 wherein the higher branched oxygenates are selected from the group consisting of C$_4$ alcohols, C$_4$ ethers, C$_4$ aldehydes, C$_4$ ethers, C$_5$ alcohols, C$_5$ aldehydes, C$_5$ ketones and mixtures thereof.

14. A process for the conversion of a feedstream comprising methanol to a C$_4^+$ alcohol product stream comprising isobutanol by aldol condensation, said process comprising contacting said feedstream at reaction conditions including a reaction pressure ranging between atmospheric and about 200 kPa and a weight hour space velocity of about 0.05 to about 10 hr$^{-1}$, and a reaction temperature between about 300° and about 400° C. with a solid catalyst comprising:
   a mixed metal oxide base comprising zinc oxide, manganese oxide, and zirconium oxide; and an activator metal selected from the group consisting of palladium, platinum, silver, rhodium, cobalt, and mixtures thereof;
   wherein the mixed metal oxides base is co-precipitated with an alkali or alkaline earth metal to provide a precipitate, the precipitate is calcined in air to provide a calcined precipitate and the calcined precipitate is impregnated with 0.2 to 5.0 wt-% of said activator metal.

15. The process of claim 11 further comprising carrying out said contacting in the presence of a diluent selected from the group consisting of carbon monoxide, carbon dioxide, hydrogen, nitrogen, and mixtures thereof.

* * * * *